US007988636B2

(12) United States Patent
Ye et al.

(10) Patent No.: US 7,988,636 B2
(45) Date of Patent: Aug. 2, 2011

(54) NON-INVASIVE ELECTRONIC APPARATUS FOR MEASURING BLOOD PRESSURE

(75) Inventors: Jilun Ye, Shenzhen (CN); Bo Tao, Shenzhen (CN); Shenyan Yu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 174 days.

(21) Appl. No.: 12/140,117

(22) Filed: Jun. 16, 2008

(65) Prior Publication Data

US 2010/0094145 A1    Apr. 15, 2010

Related U.S. Application Data

(62) Division of application No. 11/312,815, filed on Dec. 20, 2005, now Pat. No. 7,468,038.

(51) Int. Cl.
*A61B 5/02* (2006.01)

(52) U.S. Cl. ...................................................... 600/490

(58) Field of Classification Search .................. 600/490, 600/493–496, 500
See application file for complete search history.

(56) References Cited

U.S. PATENT DOCUMENTS

| 3,349,763 | A | * | 10/1967 | Clements, Jr. et al. | ........ | 600/493 |
| 3,480,005 | A | * | 11/1969 | Edwards | ........................ | 600/493 |
| 4,625,277 | A | | 11/1986 | Pearce et al. | | |
| 4,841,980 | A | | 6/1989 | Lee | | |
| 4,889,132 | A | * | 12/1989 | Hutcheson et al. | ............ | 600/493 |
| 5,224,484 | A | * | 7/1993 | Newell | ........................... | 600/493 |
| 5,704,362 | A | | 1/1998 | Hersh et al. | | |
| 5,876,359 | A | | 3/1999 | Bock et al. | | |
| 6,394,959 | B1 | | 5/2002 | Takaya | | |
| 7,468,038 | B2 | | 12/2008 | Ye et al. | | |
| 2003/0093001 | A1 | * | 5/2003 | Martikainen | .................. | 600/499 |
| 2006/0052712 | A1 | * | 3/2006 | Poliac et al. | .................. | 600/490 |
| 2009/0137913 | A1 | | 5/2009 | Ye et al. | | |

FOREIGN PATENT DOCUMENTS

CN    1098277    2/1995

OTHER PUBLICATIONS

Office Action mailed Apr. 2, 2008 in U.S. Appl. No. 11/312,815, filed Dec. 20, 2005.
Notice of Allowance mailed Oct. 7, 2008 in U.S. Appl. No. 11/312,815, filed Dec. 20, 2005.
Office Action mailed Sep. 14, 2010 in U.S. Appl. No. 12/343,331, filed Dec. 23, 2008.
Office Action mailed Jan. 20, 2011 in U.S. Appl. No. 12/343,331, filed Dec. 23, 2008.

* cited by examiner

*Primary Examiner* — Patricia Mallari
*Assistant Examiner* — Christian Jang
(74) *Attorney, Agent, or Firm* — Kory D. Christensen; Stoel Rives LLP

(57) ABSTRACT

A 3-way solenoid valve (20) is arranged between a cuff (10) and a first pressure sensor (30), wherein the common port of the 3-way solenoid valve (20) is connected with the first pressure sensor (30), the normally open port thereof connected with the cuff (10), and the normally closed port thereof connected with the air atmosphere during zeroing process. Moreover, an independent timing circuit (45) is provided additionally. In the measurement method of the present invention, the zeroing is performed with the help of the 3-way solenoid valve (20). Once a state of overtime or overpressure occurs, an air pump (50) is immediately closed, and a quick-deflation solenoid valve (60) is opened so that the pressure in the cuff (10) is released to ensure safe application.

8 Claims, 9 Drawing Sheets

ND-INVASIVE ELECTRONIC APPARATUS FOR MEASURING BLOOD PRESSURE

CROSS-REFERENCE TO RELATED APPLICATIONS

This application is a divisional of U.S. patent application Ser. No. 11/312,815, filed Dec. 20, 2005, which is incorporated herein by reference.

FIELD OF THE INVENTION

The present invention relates to a method and an apparatus for measuring blood-pressure and pulse rate for diagnosis, and particularly to a non-invasive electronic method and apparatus for measuring blood pressure which can correctly calibrate zero pressure, and process the data acquired during electronic blood pressure measurement by an algorithm of fitting for recovering a trend envelope of oscillating PW (i.e. pulse wave).

BACKGROUND OF THE ART

The non-invasive methods for measuring blood pressure in prior art employ the oscillometric method on the basis of cuff PW. The non-invasive method for measuring the blood pressure of human body mainly comprises an auscultatory method using Korotkoff sound (simply referred as Korotkoff sound method) and proportional coefficient method using cuff oscillating wave (simply referred as oscillometric method).

Korotkoff Sound method means that, the experienced medical personnel use a stethoscope, a mercury pressure gauge, a cuff and an inflation/deflation bag, wind the cuff around a proper position of an upper arm of the living body on examination, press the stethoscope close to the humeral artery, inflate the cuff via the inflation/deflation bag to increase the pressure until the block of the blood flow, and then release the cuff pressure step by step via the inflation/deflation bag to recover the blood flow in the arm. During the deflation process, the experienced medical personnel can hear the Korotkoff sound through the stethoscope and mercury pressure gauge, which changes from small to large and then from large to small due to the blood flow pulse in the artery of the arm during the deflation process, and thereby can determine the systolic pressure and diastolic pressure. While the software in the system performs the inflation and deflation control mentioned above, it also identifies the cuff pressure and PW within the cuff detected in respective steps during the deflation process with the characteristic wave, and recovers the trend envelope curve of the cuff oscillating wave on the basis of such characteristic PW. The recover methods of different facilities may differ from each other. Since the recover method has a direct effect on the formation of the envelope curve, it will to a large extent determine the accuracy of measuring the blood pressure of human body. The method widely used nowadays refers to recovery of the PW amplitude value between steps by linear interpolation method, elimination of abnormal fluctuations by multi-point moving average method, and thereby acquisition of envelope curve of the PW amplitude by linear fitting.

The method for measuring the blood pressure based on oscillometric method is currently applied to most of the electronic apparatus for measuring blood pressure. The basic process of this oscillometric method is quite similar to that of auscultatory method, that is, increasing the cuff pressure by inflation to block the blood flow in the arm, reducing the cuff pressure gradually by deflation to recover the blood flow in the ram, and detecting the static state pressure in the cuff and pressure pulse wave (PPW) due to the pulse of the artery blood. However, the calculation of blood pressure in this measuring apparatus is achieved by the following steps of: detecting the PPW in the cuff generated by the change in artery blood pulse of the arm during the deflation process and the corresponding cuff pressure, wherein a set of PPW with the amplitude varying from small to large and vice versa and a corresponding cuff pressure varying from large to small can be detected; then, taking the cuff pressure corresponding to the maximum value of the PPW as an average pressure and utilizing the empirical value for the amplitude proportional coefficient of the PPW to estimate the systolic pressure directed to a higher cuff pressure and the diastolic pressure directed to a lower cuff pressure (in short, the proportional coefficient method based on cuff oscillating pulse amplitude). The systolic pressure and the diastolic pressure can be obtained by multiplying the maximum value of the PPW by two coefficients smaller than 1.

The electronic apparatus for measuring blood pressure generally comprises the followings: (i) a pressure sensor for detecting cuff pressure and a processing circuit, (ii) a PPW processing circuit based on the change in the cuff pressure, (iii) an overpressure sensor as well as an amplification circuit and a protection processing circuit, (iv) a cuff, a control deflation valve, an air pump, gas path connected to the pressure sensor, and an inflation/deflation control section, (v) A/D converter and a single chip system, and (vi) power supply portion. During the measurement process, the detection of PPW and the cuff pressure can be performed during the deflation stage following inflation or during the inflation stage. During the deflation stage, the deflation may be continuously uniform mode (i.e. uniformly decreasing the pressure by 3-5 mmHg while detecting the PPW at the meantime). Alternatively, the deflation may also be stepwise (i.e. gradually reducing the cuff pressure by a step of 5-10 mmHg, and detecting the PPW at each pressure step), in which the magnitude of stepwise reduction of pressure is determined by the detected amplitude of the PPW. Continuously uniform deflation leads to time increase for blood pressure measurement, and it is hard to overcome an influence on the arm movement and the body position change, which would limit its application. However, stepwise deflation leads to time reduction for blood pressure measurement, and eliminates the disturbance resulting from the arm movement and the body position change, etc., with better anti-disturbance capability. Therefore, stepwise deflation is widely adopted in many blood pressure measurement apparatus.

As to the oscillometric method for non-invasive blood pressure measurement, the blood pressure measurement should be implemented by combination of hardware and software, wherein the hardware portions are mainly responsible for i) the amplification of the cuff pressure and the PPW signal, ii) another independent overpressure protection circuit for the cuff pressure, and iii) digital circuit part. The main drawbacks of the hardware portions are set forth as follows:

A). the detection of the cuff pressure requires a timed operation of zeroing, and at present zeroing is automatically performed under the condition that the cuff is not inflated. However, there exists circuit drift and it can not be ensured that the static pressure in the cuff during multiple blood pressure measurement process always drops to nearly "zero", which will lead to the following results: i) the possible failure in zero correction, and ii) the pressure value deviation due to the offset of zero point even in case of really zeroing. In short, an adverse effect would be exerted on the accuracy in detecting the cuff pressure.

B). In view of safety, two sets of independent timing system are required during the blood pressure measurement process to ensure the limit of measurement time. The blood pressure measurement module in the prior art generally contains a set of timing system itself, and provides an interface to connect with a timing trigger port provided externally. By means of the timing function of the upper computer, not only another set of independent timing system can be accomplished, but the safety requirement of independent timing can be met as well. However, this blood pressure module does not perform a complete safety independent timing and requires the cooperation of the upper computer, which may cause potential danger for the application of such blood pressure measurement module.

C). Since the amplitude for the PPW generated in the cuff during the actual deflation process increases from small to large, and then decreases from large to small after reaching the maximum of amplitude, an asymmetric and non-linear curve of trend envelope is thus formed. Therefore, there are the disadvantages of fitting with linear trend in that the envelope curve of the PW amplitude can not be correctly recovered, and the average pressure, the systolic pressure and the diastolic pressure can be not calculated accurately.

SUMMARY OF THE INVENTION

According to an aspect of the present invention, provided is a non-invasive electronic apparatus for measuring blood pressure, which comprises a cuff, a gas pump connected with the cuff, a first pressure sensor connected with the cuff, a second pressure sensor connected with the cuff for overpressure and overtime protection, a first solenoid valve unit for deflation, and a first microprocessor, wherein the apparatus further comprises a second solenoid valve which is connected between the cuff and the first pressure sensor.

According to the above-mentioned apparatus of the present invention, the second solenoid valve is a 3-way solenoid valve, wherein a common port of the valve is communicated with the first pressure sensor, a normally open port thereof is communicated with the cuff during measurement process, and a normally closed port thereof is communicated with atmosphere during zeroing process.

According to the above-mentioned apparatus of the present invention, the apparatus further comprises an independent timing circuit with timing function, wherein an output terminal of the circuit outputs an overtime signal to an overpressure and overtime control circuit for overpressure and overtime protection, while an input terminal thereof is connected with the first microprocessor for actuating the independent timing circuit.

According to the above-mentioned apparatus of the present invention, the independent timing circuit includes a second microprocessor having a timing and triggering function by software, wherein the second microprocessor has two I/O pins connected with two I/O pins of the first microprocessor, for receiving a time delay start instruction and a time delay stop instruction and an adult/infant setting instruction from the first microprocessor; and the second microprocessor further has another pin for outputting an overtime signal to the overpressure and overtime control circuit.

According to the above-mentioned apparatus of the present invention, the first solenoid valve unit comprises a quick-deflation solenoid valve and a slow-deflation solenoid valve which are connected with the cuff, wherein the quick-deflation solenoid valve is connected with a quick-valve driving circuit and the slow-deflation solenoid valve is connected with a slow-valve driving circuit, while each of the quick valve driving circuit and the slow-valve driving circuit is connected with the first microprocessor and the overpressure and overtime control circuit.

According to the above-mentioned apparatus of the present invention, the apparatus comprises a combined precise amplification circuit including a voltage follower, a preamplifier and an output amplifier which are connected in series, wherein the combined precise amplification circuit has an input terminal connected with an output terminal of the second pressure sensor and has an output terminal for outputting an overpressure signal to an input terminal of the overpressure and overtime control circuit. Moreover, the apparatus may further comprise a gain control and reference voltage circuit which has an output terminal connected with an input terminal of the output amplifier. The gain control and reference voltage circuit includes a digital circuit having three 2-to-1 bidirectional analog switches which have an output pin X connected with an inverting input terminal of the output amplifier, an input pin X1 connected with a reference voltage V1.25, and a pin X0 connected with a reference voltage V2.0.

According to the above-mentioned apparatus of the present invention, the apparatus further comprises a precise amplifier having an input terminal connected with an output of the first pressure sensor, wherein the precise amplifier outputs both a pulse signal amplified by a two-stage amplification circuit and a pressure signal to an A/D converter circuit. Moreover, the apparatus may further comprise a gain control and reference voltage circuit which has an output terminal connected with the two-stage amplification circuit. The two-stage amplification circuit comprises a preamplifier and a postamplifier which are connected in series, wherein an output of the preamplifier or the postamplifier is connected with a first resistor, while a second resistor is in parallel connected with or not connected with the first resistor via the gain control and reference voltage circuit, which is determined by pins A, B and C of the gain control and reference voltage circuit controlled by SETP and AN_MODE signals from the first microprocessor. Compared with the circuit design of prior art, the first advantage of the present invention is that the connection structure of the gas path is optimized, and the automatic and accurate "zero pressure point" calibration of the cuff pressure is performed without the influence of the residual pressure in the gas path, which improves the accuracy of the measurement of cuff pressure.

The second advantage is that, the independent timing can be performed by means of a set of independent timing circuit, which can really implement the independent timing in the module level and improve the safety during measuring of blood pressure.

The third advantage is that, with the method according to the present invention, the envelope curve of the PW amplitude trend can be recovered accurately, and the obtained average pressure shows higher degree of agreement with the real situation in clinic.

DETAILED DESCRIPTION OF THE PREFERRED EMBODIMENTS

Figure 1:
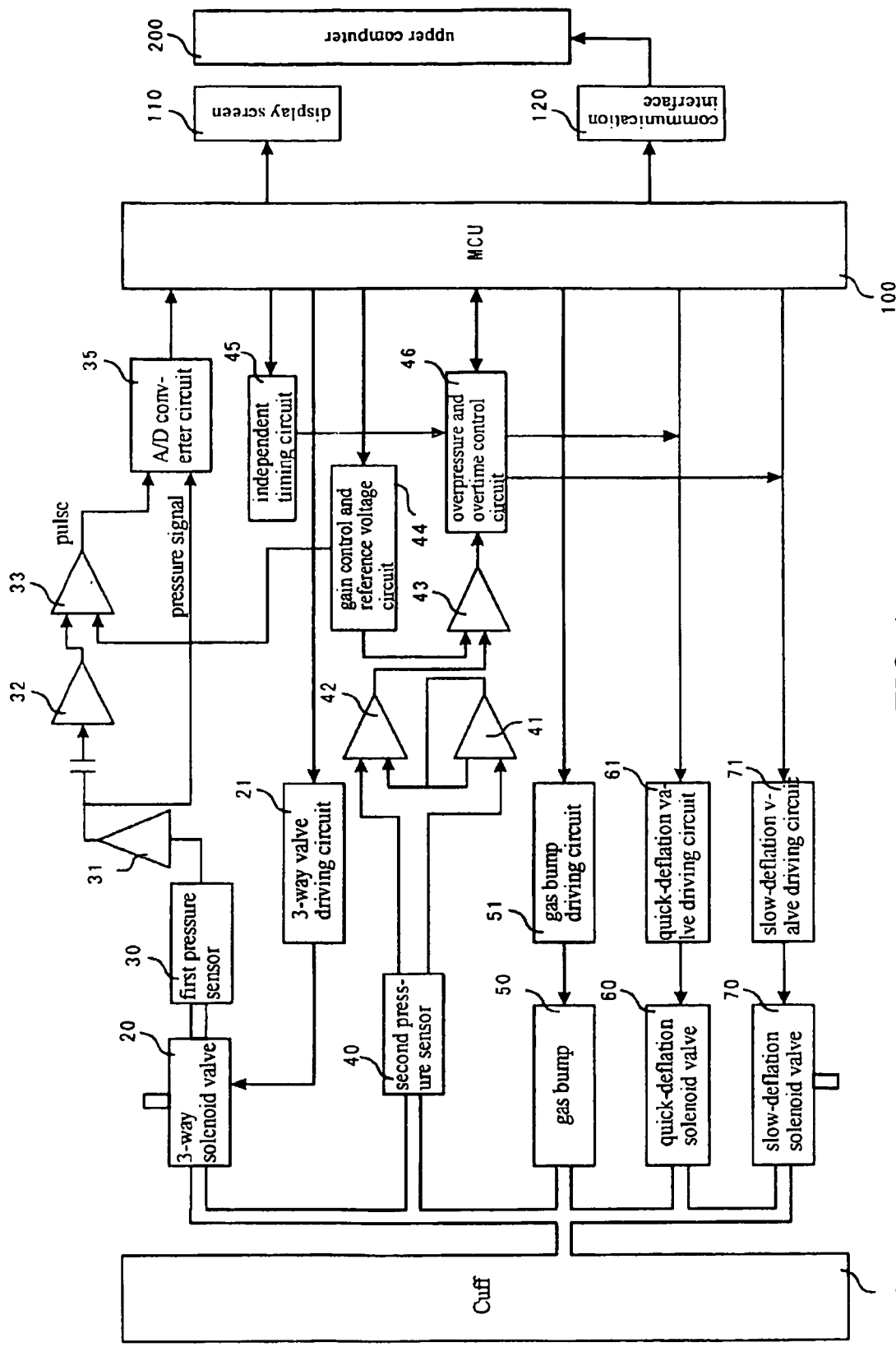
FIG. 1 is a block diagram showing the construction principles of the method and apparatus according to the present invention.
Figure 2:
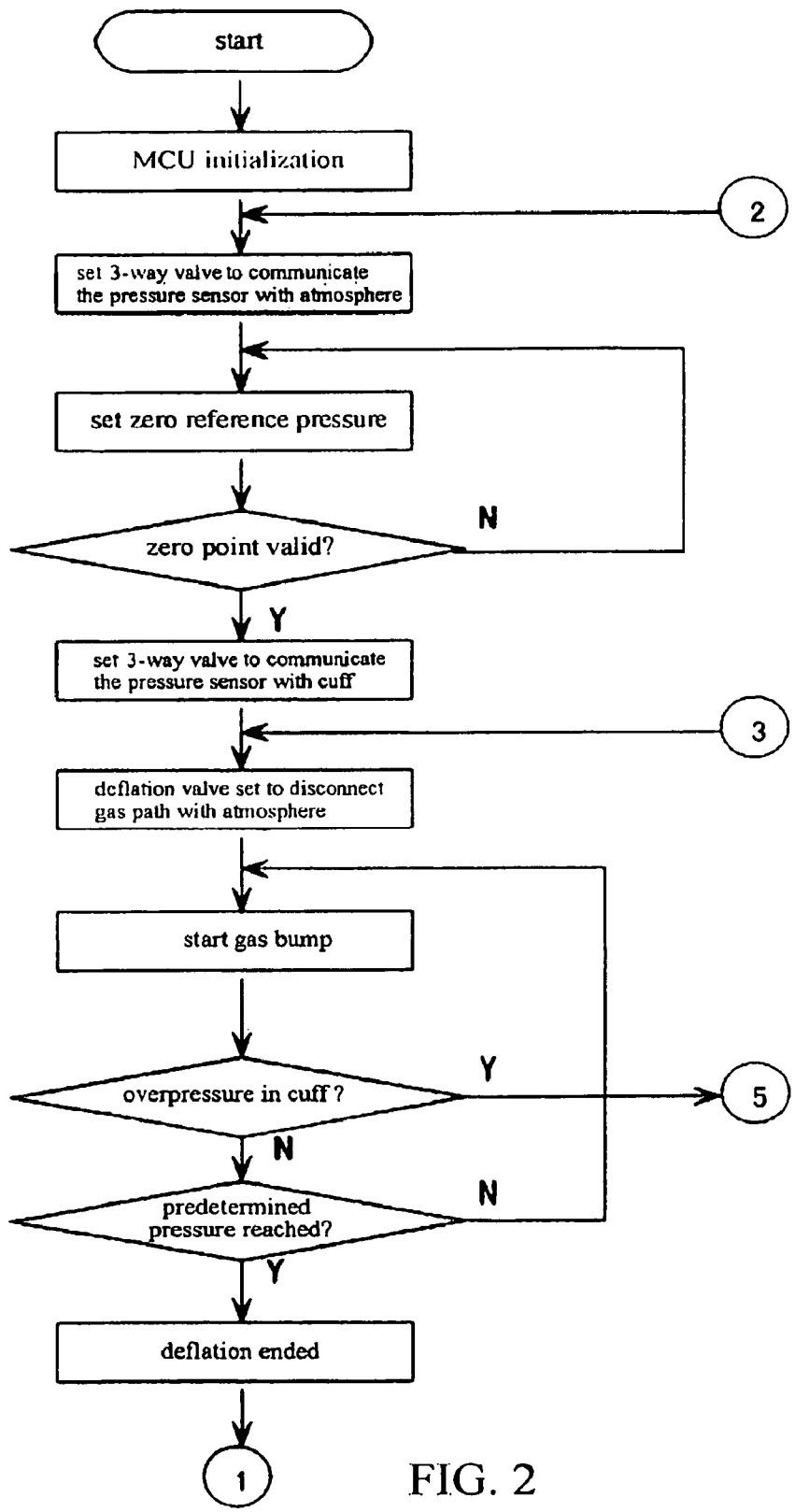
FIG. 2, FIG. 3, and FIG. 4 are flow charts representing the methods according to the present invention.
Figure 3:
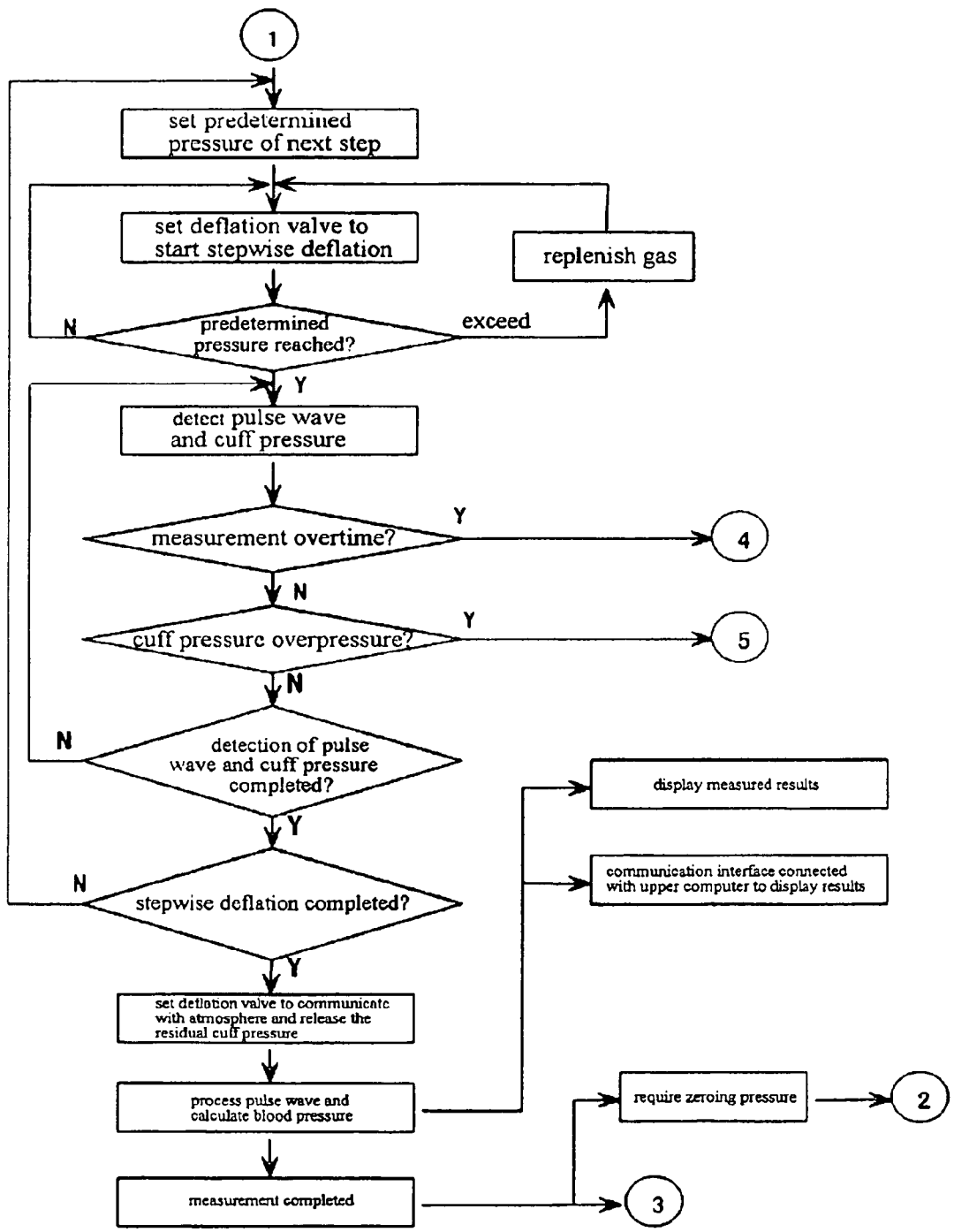
Figure 4:
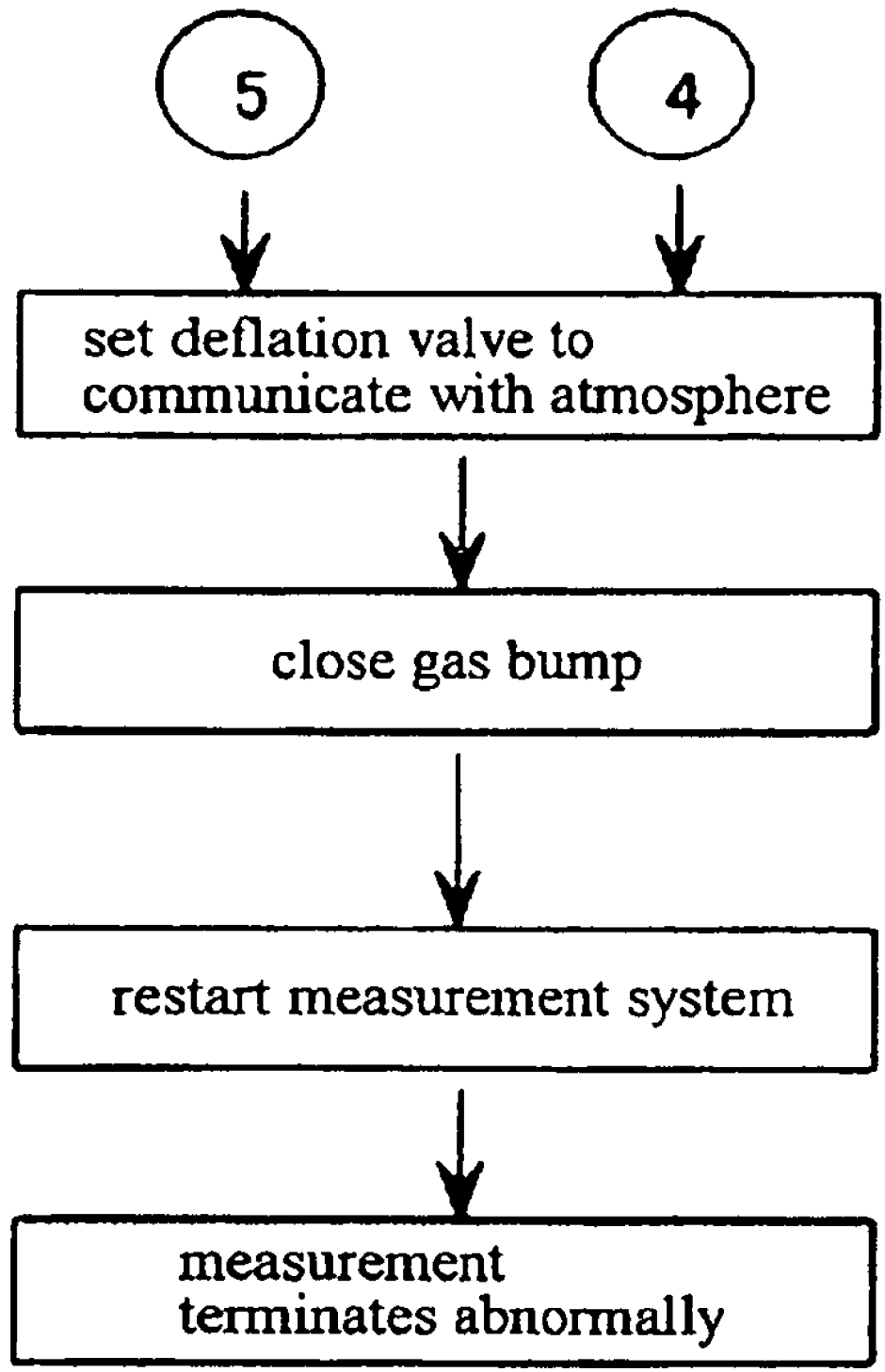

A non-invasive electronic method for measuring blood pressure according to the present invention includes the following steps:

i. inflating a cuff communicated with a first pressure sensor which has been zeroed, and then stopping inflation after a cuff pressure reaches a preset value;

ii. deflating the cuff at a preset speed and detecting whether a pulse signal occurs;

iii. after the pulse signal is detected, processing data with an algorithm for recovering a trend envelope of an oscillating pulse wave, and displaying the measured blood pressure;

during the step i, the first pressure sensor is zeroed in a state of communicating with atmosphere; and during the step iii, the algorithm for recovering the trend envelope of the oscillating pulse wave is a nonlinear fitting algorithm.

In the non-invasive electronic method for measuring blood pressure according to the present invention, zeroing operation may be performed periodically or prior to every measurement process. In this method, a solenoid valve (e.g. 3-way solenoid valve) is used so that the first pressure sensor is communicated with atmosphere during the zeroing process, but communicated with the cuff during the measurement process.

The present invention will hereinafter be further described in details on the basis of preferred embodiments with reference to the accompanying drawings.

As shown in FIG. 1~4, a non-invasive electronic method for measuring blood pressure, is based on a system comprising a cuff 10, an air pump 50, a first pressure sensor 30, a second pressure sensor 40, a quick-deflation solenoid valve 60, a slow-deflation solenoid valve 70, a first microprocessor (i.e. a primary MCU) 100, a display screen 110, a communication interface 120, and an upper computer 200. In this system, a 3-way solenoid valve 20 is provided between the cuff 20 and the first pressure sensor 30. The method includes the following steps:

a. then, when the system is powered to start operation, the solenoid valve 20 is operated in a state wherein the first pressure sensor 30 is communicated with the atmosphere, and then performs zeroing;

b. once the zeroing is done, the solenoid valve 20 is operated in a state wherein the first pressure sensor 30 is communicated with the cuff 10; thereby, during the blood pressure measurement process, the air pump 50 is operated to increase the pressure in the cuff 10; the upper computer 200 receives the data via the communication interface 120 and displays the pressure in the cuff 10, or the pressure in the cuff 10 is shown on the display screen 110; and the inflation process is stopped when the pressure in the cuff 10 reaches a pre-determined value;

c. the system adjusts (opens/closes) the quick-deflation solenoid valve 60 and slow-deflation solenoid valve 70 to deflate the cuff 10 at a preset rate, and detects whether there is pulse signal;

d. once the pulse signal is detected, the primary MCU 100 processes the data with the algorithm decided by the firmware through non-linear fitting to recover the trend envelope of the oscillating PW, and the detected blood pressure value is displayed on the display screen 110 or the upper computer 200;

e. when the phenomena of overtime or overpressure occurs during the measurement process procedure, the system immediately closes the air pump 50, and open the quick-deflation solenoid valve 60 to release the pressure in the cuff 10 so as to ensure safe application; meanwhile, the system also resets the primary MCU 100;

f. once the measurement process is completed, the quick-deflation solenoid valve 60 is opened to release the pressure in the cuff 10, and then the quick-deflation solenoid valve 60 is closed;

g. when the blood pressure measurement is carried out for the second time, repetition of steps starts from step c, or starts from step b periodically.

The 3-way solenoid valve 20 has a common port communicated with the first pressure sensor 30, a normally open port communicated with the cuff during measurement process, and a normally closed port thereof is communicated with atmosphere during zeroing process. The 3-way solenoid valve 20 is driven by a 3-way solenoid valve drive circuit 21 controlled by the primary MCU 100. The primary MCU 100 outputs a high level and a low level for controlling the 3-way valve drive control circuit 21, so that the solenoid valve 20 is operated in a state wherein the common port is communicated with the normally open port and not communicated with the normally closed port, and a state wherein the common port is communicated with the normally closed port and blocked from the normally open port.

Figure 5:
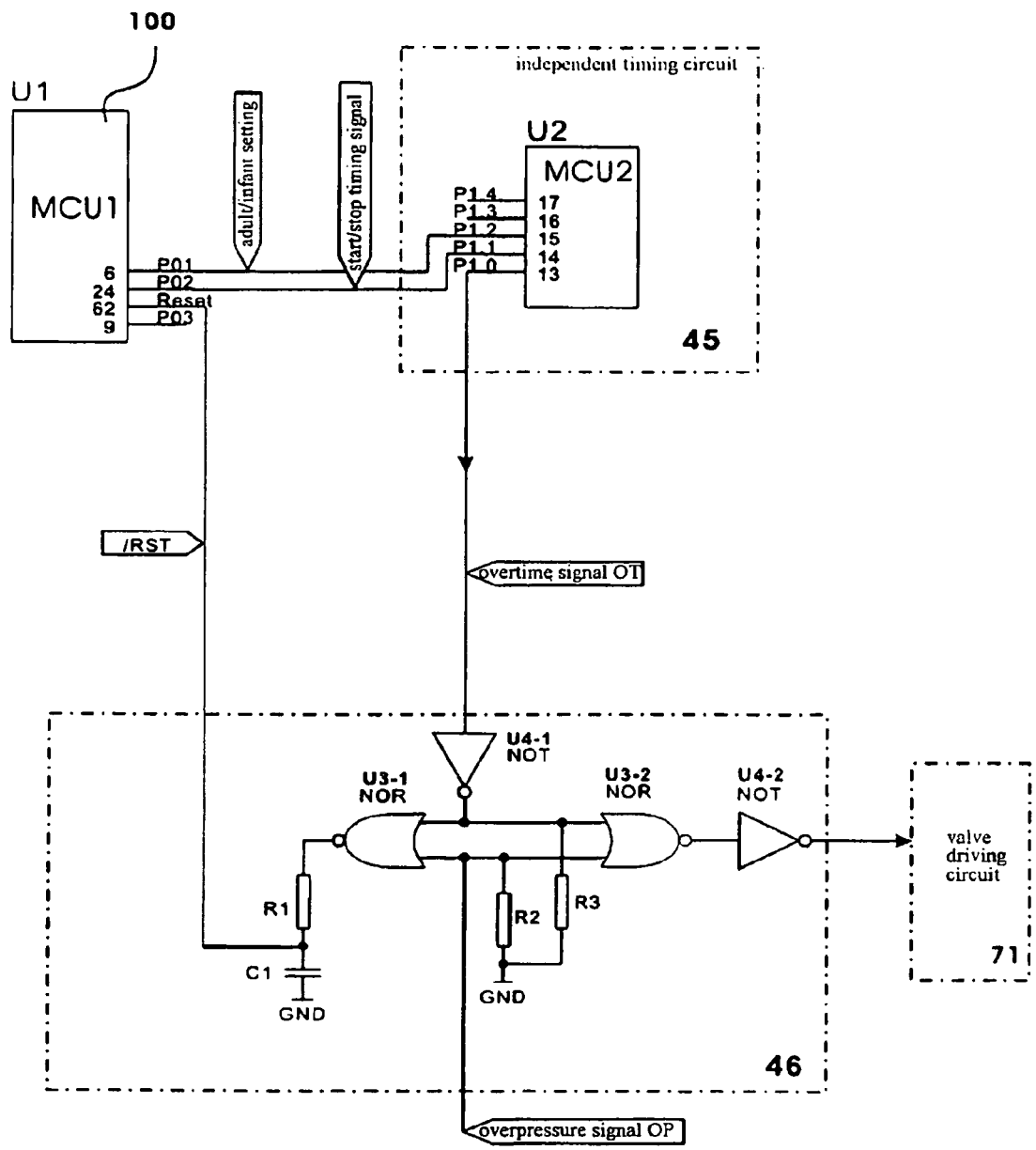
FIG. 5 is an electric principle diagram of the independent timing circuit in the apparatus according to the present invention.

With reference to FIGS. 1 and 5, during the measurement process of step f in the non-invasive method, once the state of the overtime or overpressure occurs, the system immediately closes the air pump 50 and opens the quick-deflation solenoid valve 60. The step f is performed in such a manner that an independent timing circuit 45 is provided in the system, wherein said independent timing circuit 45 is actuated by the primary MCU 100 so that a control signal OT is output to the overpressure and overtime control circuit 46 as soon as time is over, and then the circuit 46 immediately opens the quick-deflation solenoid valve 60 and closes the air pump 50 to release the cuff pressure.

Figure 7:
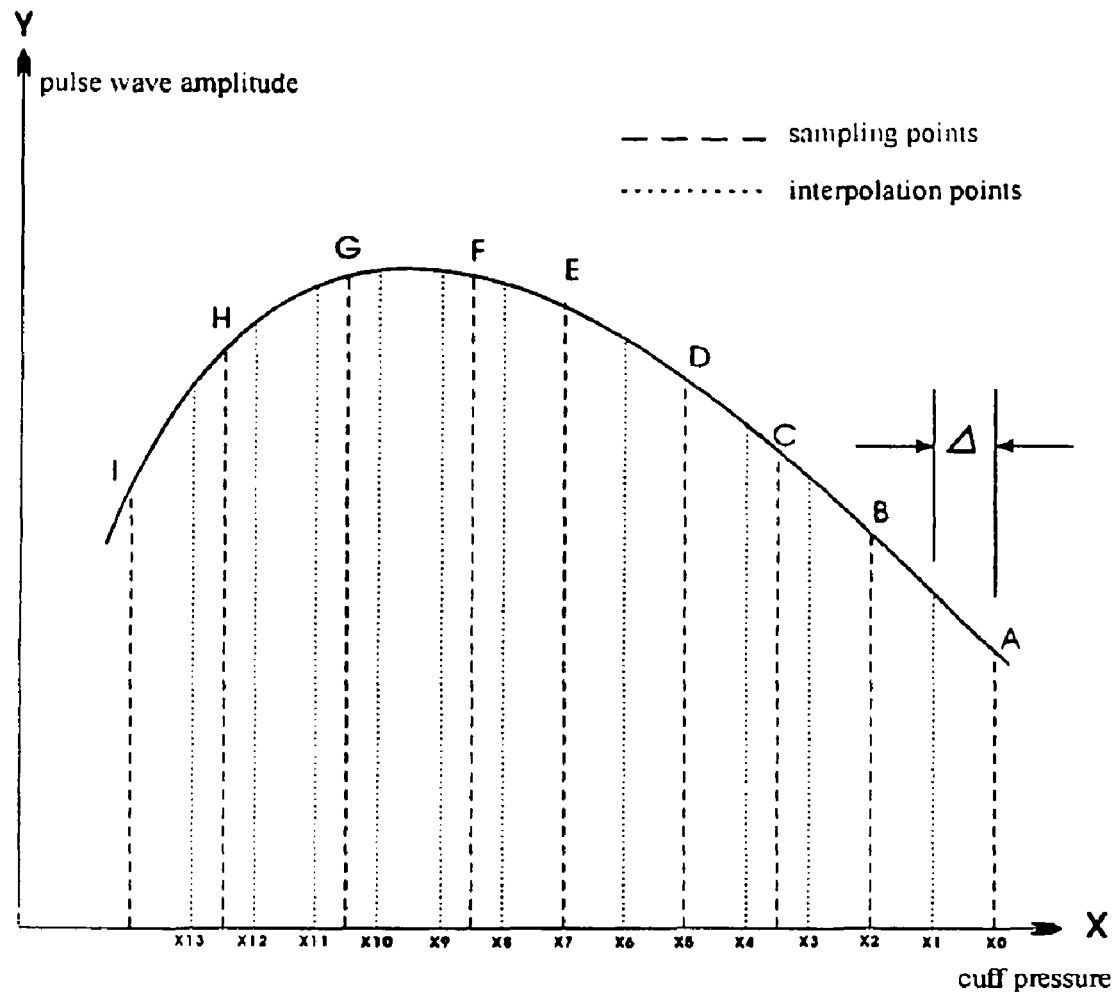
FIG. 7 is a schematic graph of trend envelope of the PW amplitude according to the present invention.
Figure 8:
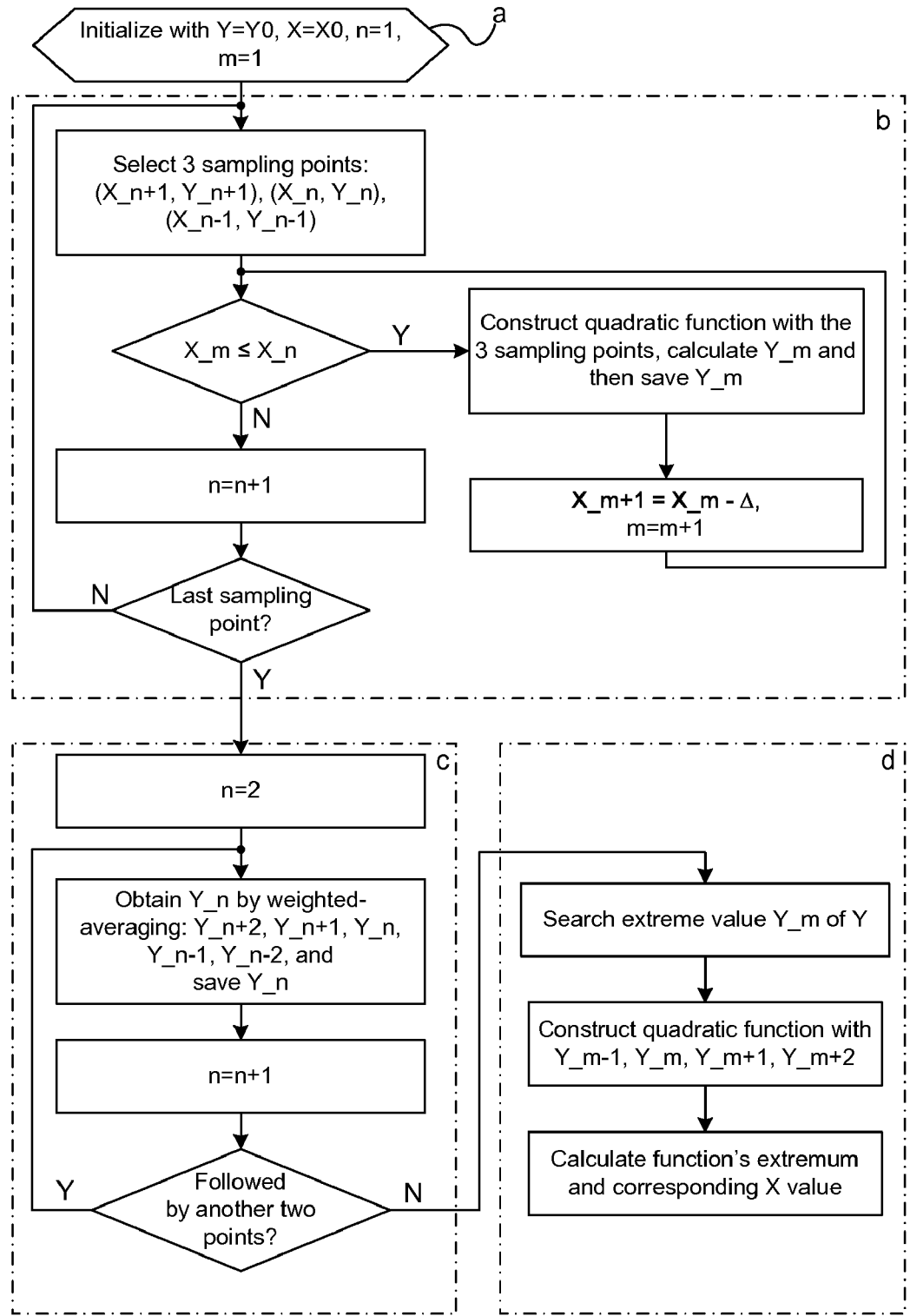
FIG. 8 is a flow chart showing the algorithm of data processing for recovering the trend envelope of the oscillating pulse wave by non-linear fitting according to the present invention.

With reference to FIGS. 7 and 8, after the cuff pressure reached the preset value by inflation process, the data processing during the step d includes the following steps:

d1: sampling during the deflation process, and thereby obtaining a cuff pressure X and a pressure pulse wave amplitude Y of each sampling point;

d2: taking a cuff pressure X0 and a pressure pulse wave amplitude Y0 of a first sampling point among the sampling points as initial values, and selecting a pressure step Δ;

d3: selecting at least three adjacent sampling points while sequentially moving point-by-point on the basis of the sampling points, and then performing data processing as follows for the sampling points until the last sampling point:

piecewise performing trend term fitting by constructing a multiple-order curve with said at least three adjacent sampling points, generating a cuff pressure Xm and a pressure pulse wave amplitude Ym of an interpolation point between two adjacent sampling points of said at least three adjacent sampling points and then saving Xm and Ym, wherein Xm is within a cuff pressure interval of said two adjacent sampling points, Xm=X0−mΔ, while each of n and m is a natural number which increases by one during such fitting process;

d4: performing smooth processing by taking said pressure pulse wave amplitude of each saved interpolation point as an intermediate value, weighted-averaging or arithmetical-averaging the amplitude of each interpolation point with amplitudes of at least two adjacent interpolation points while moving point-by-point, and thereby obtaining the smoothed amplitude of each interpolation point and then saving it; and d5: searching the maximum of pulse wave amplitude among the saved and smoothed amplitudes, constructing a multiple-order curve with the data of the point corresponding to the maximum of pulse wave amplitude and at least one point on either side thereof, and calculating the maximum of pulse wave amplitude of the multiple-order curve as the extreme value of trend envelope curve of the oscillating pulse wave, wherein a cuff pressure corresponding to the extreme value is an average pressure.

During step d3 of said algorithm by non-linear fitting to recover the trend envelope of the oscillating PW, an interpolation value of the PPW amplitude corresponding to the preset cuff pressure X0-mΔ which ranges from the cuff pressure value of every first point to that of every second point, is generated by piecewise constructing a fitted quadratic curve with the data of three adjacent sampling points point-by-point.

During step d4 of said algorithm by non-linear fitting to recover the trend envelope of the oscillating PW, the smooth processing is performed by arithmetically averaging the PW amplitude value of said saved point and the PW amplitude values of two points on either side of each saved point respectively.

During step d5 of said algorithm by non-linear fitting to recover the trend envelope of the oscillating PW, a quadratic curve is constructed with the data of the point corresponding to the maximum of PW amplitude value for reference, the data of one adjacent point along the pressure-increasing direction and the data of two adjacent point along the pressure-decreasing direction by least square procedure, and then the extreme value can be obtained from the curve.

During step d5 of said algorithm by non-linear fitting to recover the trend envelope of the oscillating PW, a quadratic curve is constructed with the data of the point corresponding to the maximum of PW amplitude for reference and the data of one adjacent point data to the left side and right side respectively, and then the extreme value can be obtained from the curve.

A non-invasive electronic apparatus for measuring blood pressure according to the present invention mainly comprises the cuff 10, the gas pump 50 connected with the cuff 10, the first pressure sensor 30 connected with the cuff 10, the second pressure sensor 40 for overpressure and overtime protection connected with the cuff 10, the first solenoid valve unit for deflation, and the first microprocessor (i.e. the primary MCU) 100. Moreover, the apparatus further comprises a second solenoid valve which is connected between the cuff 10 and the first pressure sensor 30.

In the above-mentioned apparatus of the present invention, the second solenoid valve may be a 3-way solenoid valve 20. The first solenoid valve unit may be composed of one solenoid valve, but preferably composed of the quick-deflation solenoid valve 60 and the slow-deflation solenoid valve 70.

As is shown in FIG. 1, the non-invasive electronic apparatus for measuring blood pressure according to a preferred embodiment of the above-mentioned method comprises the cuff 10, the air pump 50, the first pressure sensor 30, the second pressure sensor 40, the quick-deflation solenoid valve 60, the slow-deflation solenoid valve 70, the primary MCU 100, a display screen 110 and a communication interface 120, wherein a 3-way solenoid valve 20 is provided between the cuff 10 and the first pressure sensor 30. A common port of the valve 20 is communicated with the first pressure sensor, a normally open port thereof is communicated with the cuff during measurement process, and a normally closed port thereof is communicated with atmosphere during zeroing process.

It's also shown in FIG. 1 that, in a preferred embodiment, the quick-deflation solenoid valve 60 is electrically connected with a quick-deflation valve drive circuit 61. An input terminal of said quick-deflation valve drive circuit 61 is electrically connected with output terminals of the primary MCU 100 and the overpressure and overtime control circuit 46. An input terminal of the overpressure and overtime control circuit 46 is electrically connected with the output of the independent timing circuit 45.

As shown in FIG. 5, in a preferred embodiment, said independent timing circuit 45 comprises a second MCU U2 which is preferred to be MSP430 micro processor and performs the timing and triggering by means of software, wherein two I/O pins of said second MCU U2 are electrically connected with two I/O pins of the primary MCU 100 to receive a time delay start instruction, a time delay stop instruction and an adult/infant setting instruction from the primary MCU 100; the second MCU U2 further has a pin which outputs an overtime signal OT to the overpressure and overtime control circuit 46.

It is shown that the communication interface 120 is an RS232 interface in the preferred embodiment, but it may be a USB interface.

Figure 6A:
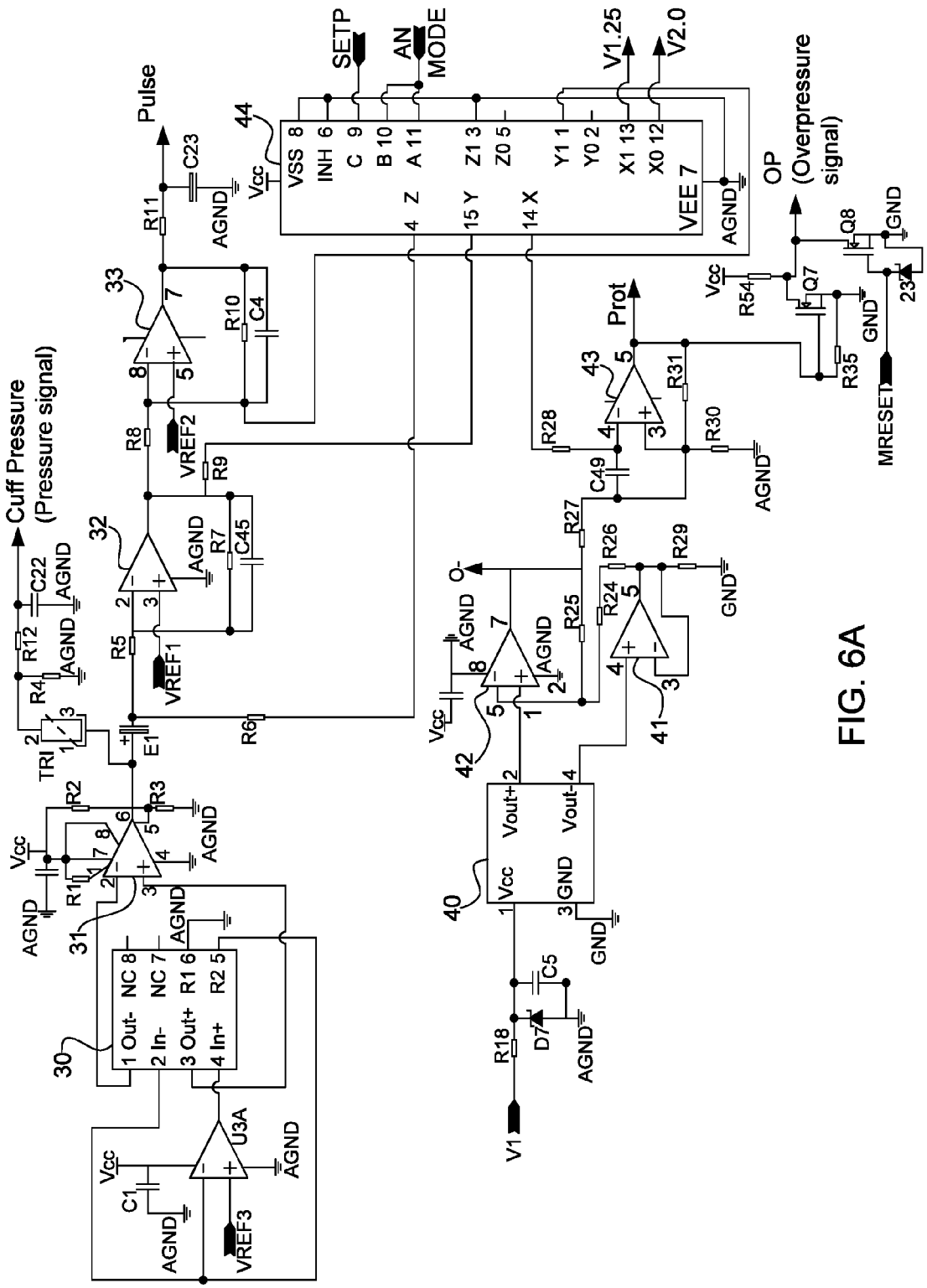
FIG. 6A is an electric principle diagram of the sensor and the amplifier circuit in the apparatus according to the present invention.

As shown in FIGS. 6 and 1, the output of said first pressure sensor 30 is electrically connected to a precise amplifier circuit 31. One of the outputs of the precise amplifier circuit 31 is input to an A/D converter circuit 35 as a pressure signal CUFFPRESS, while the other output is also input to the A/D converter circuit 35 as a pulse signal PULSEWAVE after being amplified by a preamplifier 32 and a postamplifier 33.

The output of the first pressure sensor 30 is connected with a port 2 and a port 3 of the precise amplifier 31, while an input pin 4 of the first pressure sensor 30 is connected with port 7 of an operational amplifier U3A. Both a pin 2 and a pin 5 of the first pressure sensor 30 in parallel are connected with port 8 of the operational amplifier U3A, wherein a pin 2 of the operational amplifier U3A is grounded, and a pin 6 of the operational amplifier U3A is connected with a power source Vcc and grounded with AGND via a capacitor C1. In addition, a pin 6 of the first pressure sensor 30 is grounded. For amplifier 31, a pin 1 is connected with a resistor R1 and then connected with a pin 8; a pin 7 is connected with a power source Vcc and grounded via a capacitor C44; a pin 4 is grounded; a pin 5 is connected between resistors R2 and R3. Meanwhile, the other end of the resistor R2 is connected with Vcc and the other end of R3 is grounded. Moreover, an output pin 6 of the precise amplifier 31 is divided into two routes, wherein one of routes outputs the partial voltage to a resistor R12 via series connection of a potentiometer TR1 with a resistor R4 and is further grounded via a capacitor C22 and outputs the pressure signal CuffPress, the other of routes is connected with a resistor R5 via a stopping capacitor E1 and is further output to the preamplifier 32 via the resistor R5. At the same time, programmable gain selection is performed for the preamplifier 32, so that different gains are set in different application modes (adult/infant).

In the preferred embodiment, the preamplifier 32 comprises an input resistor R5, and an additional resistor R6 which is in parallel connection with the input resistor R5 through a gain control and reference voltage circuit 44 or not in parallel connection with the input resistor, wherein whether the resistor R6 is in parallel connection with the input resistor R5 is determined by pins A, B and C of the gain control and reference voltage circuit 44 under the control of SETP signal and AN_MODE signal of the primary MCU 100.

The postamplifier 33 also comprises an input resistor R8, and an additional resistor R9 which is in parallel connected with the input resistor R8 through the gain control and reference voltage circuit 44 or not connected with the input resistor R8, wherein whether resistor R9 is in parallel connected with resistor R8 is determined by pins A, B and C of the gain control and reference voltage circuit 44 under the control of the SETP signal and the AN_MODE signal of the MCU 100. The magnitude of the input resistor determines the magnification of the amplifiers, and the primary MCU 100 determines whether the resistors R6 and R9 are in parallel connection with the input resistor R5 and R8 as required during operation.

Said gain control and reference voltage circuit 44 is mainly composed of digital circuit 4053 comprising three 2-to-1 bidirectional analog switches. As to the digital circuit 4053, the control pins A, B, and C are connected with the primary MCU 100, while an output pin X thereof is connected with an inverting input terminal of the output amplifier 43 via a resistor R28, an input pin X1 is connected with reference voltage V1.25 and an pin X0 with reference voltage V2.0. Thereby, different reference voltages lead to different thresholds of the output amplifier 43. In addition, pins 7, 8, and 6 of the digital circuit 4053 comprising analog switches are grounded with AGND; a pin 9 is for receiving SETP signal from a port of CPU to perform the connection/disconnection of pin 4 with pin 3 or 5; pins 10 and 11 are in parallel connected with each other for receiving AN_MODE signal from a port of CPU to perform the synchronous switching of connecting pin 15 with pin 1 or 2 and connecting pin 14 with pin 13 or 12.

As shown in FIG. 1, FIGS. 6A-6C and FIG. 5, an output of said second pressure sensor 40 is connected with the voltage follower constituted by an amplifier 41 and the preamplifier constituted by an amplifier 42. The output of the amplifier 42 and an output "X" of the gain control and reference voltage circuit 44 are respectively connected with two input terminals of the output amplifier 43, while the output terminal of the output amplifier 43 outputs as the overpressure signal OP after being driven by FET Q7 and the overpressure signal OP is input to the overpressure and overtime control circuit 46, thereby to ensure the safety of living body by detecting whether the cuff pressure exceeds the preset protective pressure point.

The overpressure protection is performed by the followings. A pin 1 of the second pressure sensor 40 is connected with a power input VI via R18. Both a voltage-regulator diode D7 and a capacitor C5 in parallel are grounded AGND, while a pin 3 of the second pressure sensor 40 is also connected with ground AGND. Furthermore, a pin 4 of the second pressure sensor 40 is connected with a pin 3 of the amplifier 41, wherein a pin 4 of the amplifier 41 is connected with pin 5 and further connected with pin 8 of the amplifier 42 via the series connection of a resistor R26, a resistor R24 and a potentiometer TR2. In addition, a pin 2 of the second pressure sensor 40 is connected with a pin 1 of the amplifier 42, wherein a pin 8 of the amplifier 42 is connected with a pin 7 via a resistor R25, said pin 7 is connected with a pin 4 of output amplifier 43 via a resistor R27. Said pin 4 of the output amplifier 43 is connected with a pin 14 of the digital circuit 4053 via a resistor R28 and further connected with reference voltage V1.25 and V2.5 via pin 13 or 12 of the digital circuit 4053. Moreover, a pin 5 of the amplifier 42 is grounded GND via a resistor R29, while a pin 3 of the output amplifier 43 is grounded GND and connected with a pin 5 thereof via resistors R31; pins 3 and 4 of the output amplifier 43 are connected with each other via a capacitor C49. Meanwhile, a pin 5 of the output amplifier 43 is connected with pin 1 of FET Q7, wherein a pin 1 of FET Q7 is also connected with a pin 2 thereof via resistor R35 and grounded AGND, and a pin 3 of FET Q7 is connected with power source Vcc via a resistor R54 and also outputs the overpressure signal OP.

One route of the output of the second pressure sensor 40 is connected with the voltage follower constituted by the amplifier 41, and the output of the voltage follower is connected with an inverting input terminal of the amplifier 42. Meanwhile, the other route of output of the second pressure sensor 40 is connected with the in-phase input terminal of the amplifier 42 to perform the pre-amplification of the static cuff pressure. Furthermore, the output terminal of such amplification circuit is connected with the in-phase input terminal of the output amplifier 43, while the inverting input terminal of output amplifier 43 is input with adjustable reference voltage, thereby realizing the correct state reversion of overpressure protection point to meet the requirement of setting different overpressure protection points under different application modes.

Figure 6C:
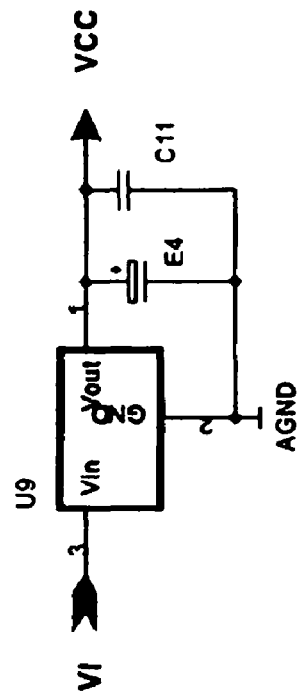
FIG. 6B and FIG. 6C are diagrams showing circuits for providing reference voltage VREF and VCC.
Figure 6B:
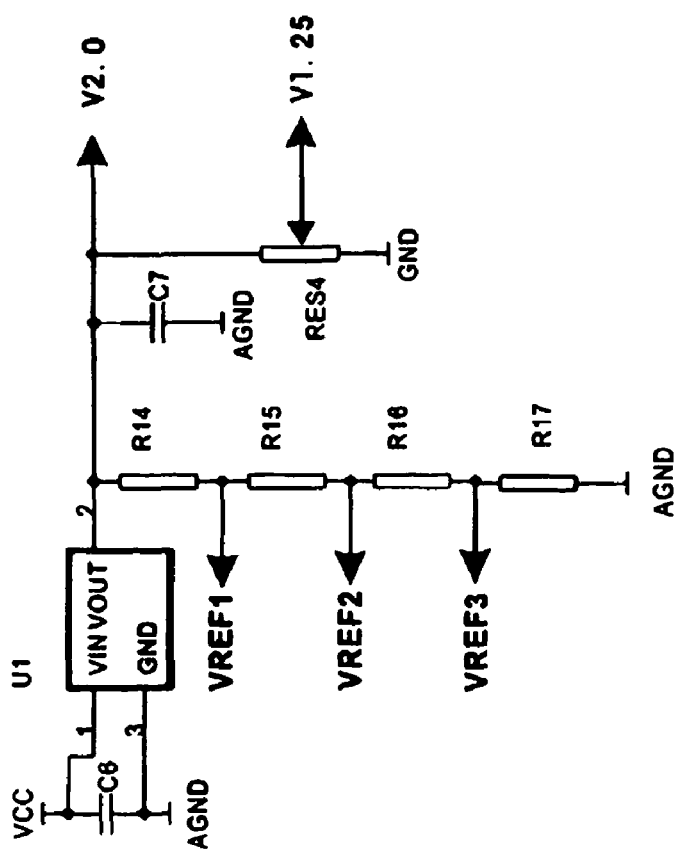

FIG. 6B shows a circuit for providing reference voltage VREF1, VREF2 and VREF3; and FIG. 6C shows a circuit for providing reference voltage VCC.

As shown in FIG. 5 and FIG. 1, said overpressure and overtime control circuit 46 includes the inverters U4-1, U4-2 and NOR gate digital circuits U3-1, U3-2. An input terminal of the overpressure and overtime control circuit 46 receives the overtime signal OT output by the independent timing circuit 45 and the overpressure signal OP output by the output amplifier 43, while an output terminal of the circuit 46 is connected with the quick-deflation valve drive circuit 61 and slow-deflation valve drive circuit 71.

The communication interface 120 is an RS232 interface in the preferred embodiment, but it may also be a USB interface in other embodiments.

In the preferred embodiment shown in FIG. 5, an input terminal of said independent timing circuit 45 for starting timing is connected with a port P02 of the primary MCU 100. The second MCU U2 shown in the Figure is structured by a single-chip of TI's MSP430, and timing is performed by the system software of MSP430. The software timer is enabled when the second MCU U2 detects the signal of enabling the timer, and the software timer is stopped when the second MCU U2 detects the signal of the stopping timer. The time limit of such software timer depends on the application mode settings for adult/infant, wherein the time limit is 180±1 seconds for adult mode and 90±1 seconds for infant mode.

Certainly, the timer discussed above can also use an analog device or digital circuit to fulfill the same functions.

In the preferred embodiment of the present invention, I/O port P1.0 of the MCU U2 is connected with the input terminal of the overtime control circuit 46. The I/O port is maintained at a low level when the system is in standby state rather than in measurement state. However, when the system is in measurement state, the I/O port outputs a high level and is maintained at this level until the measurement process is completed and then again outputs a low level to maintain the standby state. When one of the input terminals of the overtime control circuit 46 is at a low level, the timer stays in a state of stopping timing. Only when timing of the timer exceeds the time limit (e.g. 180±1 seconds (for adult) or 90±1 seconds (for infant)), does the input terminal output signals to actuate the deflation solenoid valve 70, stop the air pump 50, and notify the primary MCU 100.

The firmware within the primary MCU 100 is responsible for the measurement, data processing, result calculation, and communication with the upper control system during the measurement process. During the measurement process, the cuff pressure is increased to a preset value by boosting the pressure via the gas path, and then the cuff is deflated under the control of the software. During the deflation, the PPW amplitude and corresponding cuff pressure value are obtained for each sampling point at the same time, wherein the deflation may be in stepwise mode or a continuous mode. As shown in FIG. 7, in the condition that the cuff pressure is used as the horizontal axis and the PW amplitude is used as the vertical axis, there are discrete data points $A(X_A, Y_A)$, $B(X_B, Y_B)$, $C(X_C, Y_C)$ . . . , wherein $X_A$, $X_B$, $X_C$ . . . are sampled values of the cuff pressure with non-uniform difference. For the sake of convenient calculation and fine fitting, during recovering the curve envelope by fitting, non-linear interpolation is performed in this method of the present invention, so that a series of data points (X0,Y0), (X1,Y1), (X2,Y2), (X3,Y3) . . . with uniform pressure difference which represent the curve envelope, in which X1−X0=X2−X1=X3−X2=. . . =Δ, and then the data points are processed by calculation.

As shown in FIG. 8, the detailed processing flow comprises the following steps:

a. taking cuff pressure of the first sampling point (X0,Y0) as the initial value, and selecting a pressure step Δ which is used later to produce data for an interpolation point $(X_m, Y_m)$ by subsequent trend term fitting with each sampling point $(X_n, Y_n)$ as the intermediate value, where n, m are natural number, and $X_m = X0 - m\Delta$;

b. on the basis of said sampling points, selecting a set of at least 3 adjacent sampling points by sequentially moving the sampling points point-by-point, and then performing piecewise trend term fitting by constructing a multiple-order curve with said at least 3 points; during the cuff pressure in the range between cuff pressure of the first point and cuff pressure of the second point, the PPW amplitude Ym of interpolation points corresponding to each preset cuff pressure interpolation X0-mΔ within a range between the cuff pressure of the first point and the cuff pressure of the second point are generated and saved in turn; and n, m increase by one during this process;

c. smooth processing is carried out by taking said PW amplitude of each saved interpolation point which has been saved as the intermediate value: said amplitude of each point is moved point-by-point so as to be weighted-averaged or arithmetical-averaged with the amplitude of at least two adjacent points; then the flattened amplitude of the point is obtained and saved;

d. searching the maximum of PW amplitude in the saved and smoothed amplitudes, taking such position for reference, selecting at least one point on either side thereof respectively to construct a multiple-order curve with the selected points, calculating the maximum value of the multiple-order curve, taking the maximum value as the extreme value of the trend envelope curve of oscillating PW, and determining the corresponding cuff pressure as average pressure.

In the above steps, the pressure step Δ in step a can be selected from the pressure difference range of 3-5 mmHg depending on the living body. The quadratic curve of in step b is fitted by three points, and can be expressed as $Y = a_n X^2 + b_n X + c_n$, where:

$$Y_n = Y(X_n), Y_{n+1} = Y(X_{n+1}), Y_{n-1} = Y(X_{n-1})$$

Thereby $a_n$, $b_n$, and $c_n$ can be determined, and data Ym at pressure of X0−mΔ≦Xn can be further calculated. If the system has sufficient resource and operation speed, a multiple-order curve can be constructed with at least 3 points and non-linear interpolation is performed.

Instead of interpolating between the first two sampling points of each segment as shown in the example, interpolation can be performed between the last two sampling points; in the case of trend term fitting with all the sampling points (Xn,Yn) as the intermediate value, since the sampling points are generally sufficient, it is allowed to give up the interpolation between the last two sampling points or the first two sampling points.

During the smooth filter processing in step c, the method of moving weight average of adjacent points is used, e.g. five points, and in practice, weight average of 3 points or 4 points can also be used. Said weight average can also be simplified into arithmetic average.

To improve the data accuracy, the above step d can be further processed, as shown in FIG. 7: according to the inquired maximum position, one adjacent data point is selected along the pressure increasing direction and two adjacent data points along the pressure decreasing direction, so that the side with sharper trend contains more data points to ensure the trend weight of the rising edge; then on the basis of 4 data points mentioned above, a quadratic curve is constructed by the least square procedure, and the peak of such curve is confirmed to be the extreme value of trend envelope of the PW amplitude, which corresponds with the average pressure; based on the extreme value of the amplitude, the corresponding amplitude of systolic pressure and diastolic pressure can be further calculated, and thereby deriving the systolic pressure and the diastolic pressure from the envelope.

During the implementation of the present invention, the data acquisition and pre-processing program module of the system software will also carry out the identification of reference wave and the calculation and estimation of the amplitude for PW. Only when the normal trend pulse occurs, the subsequent pulse fitting and interpolation is carried out, and further calculation of the blood pressure is performed. When normal trend pulse is not found, the module continues finding PW or report abnormality and produces corresponding error information, which is not described here since it is beyond the scope of the present invention.

It has been proved that the present invention optimizes the connection structure of the gas path, and that automatic and accurate "zero pressure point" calibration of the cuff pressure is performed without the influence of the residual pressure in the gas path, which improves the accuracy of the measurement of cuff pressure.

Furthermore, the independent time-limiting timing function can be performed by means of a set of independent timing circuit, which can really perform the independent timing in the module level and improve the safety during measurement of blood pressure.

In the present invention, the trend envelope of oscillating PW is recovered by non-linear fitting, which can obtain both the maximum value of the PW and the average pressure. The obtained average pressure is proved to show higher degree of agreement with the real situation in clinic. In particular, the data obtained by stepwise deflation can be processed effectively, which shortens the measurement process and helps to improve the safety.

While specific embodiments and applications of the present invention have been illustrated and described, it is to be understood that the invention is not limited to the precise configuration and components disclosed herein. Various modifications, changes, and variations apparent to those of skill in the art may be made in the arrangement, operation, and details of the methods and systems of the present invention disclosed herein without departing from the spirit and scope of the present invention.

What is claimed is:

1. A non-invasive electronic apparatus for measuring blood pressure, which comprises a cuff, a gas pump connected with the cuff, a first pressure sensor connected with the cuff, a second pressure sensor connected with the cuff for overpressure and overtime protection, a first solenoid valve unit for deflation, a first microprocessor, a second solenoid valve which is connected between the cuff and the first pressure sensor, an independent timing circuit with timing function, and a combined precise amplification circuit including a voltage follower, a preamplifier, and an output amplifier, wherein an output terminal of the timing circuit outputs an overtime signal to an overpressure and overtime control circuit for overpressure and overtime protection while an input terminal thereof is connected with the first microprocessor for actuating the independent timing circuit, wherein the voltage follower has an input terminal connected with an output terminal of the second pressure sensor, the preamplifier has an input terminal connected with an output terminal of the voltage follower and an input terminal connected with the output terminal of the second pressure sensor, and the output amplifier has an input terminal connected with an output terminal of the preamplifier and an input terminal connected with a reference voltage signal, the output amplifier being configured to output an overpressure signal to an input terminal of the overpressure and overtime control circuit.

2. The non-invasive electronic apparatus for measuring blood pressure according to claim 1, wherein the second solenoid valve is a 3-way solenoid valve, wherein a common port of the valve is communicated with the first pressure sensor, a normally open port thereof is communicated with the cuff during measurement process, and a normally closed port thereof is communicated with atmosphere during zeroing process.

3. The non-invasive electronic apparatus for measuring blood pressure according to claim 1, wherein the independent timing circuit includes a second microprocessor having a timing and triggering function by software, wherein the second microprocessor has two I/O pins connected with two I/O pins of the first microprocessor, for receiving a time delay start instruction and a time delay stop instruction and an adult/infant setting instruction from the first microprocessor; and the second microprocessor further has another pin for outputting an overtime signal to the overpressure and overtime control circuit.

4. The non-invasive electronic apparatus for measuring blood pressure according to claim 1, wherein the first solenoid valve unit comprises a quick-deflation solenoid valve and a slow-deflation solenoid valve which are connected with the cuff, wherein the quick-deflation solenoid valve is connected with a quick-valve driving circuit and the slow-deflation solenoid valve is connected with a slow-valve driving circuit, while each of the quick-valve driving circuit and the slow-valve driving circuit is connected with the first microprocessor and the overpressure and overtime control circuit.

5. The non-invasive electronic apparatus for measuring blood pressure according to claim 1, further comprising a gain control and reference voltage circuit configured to output the reference voltage signal.

6. The non-invasive electronic apparatus for measuring blood pressure according to claim 5, wherein the gain control and reference voltage circuit includes a digital circuit having three 2-to-1 bidirectional analog switches which have an output pin X connected with an inverting input terminal of the output amplifier, an input pin X1 connected with a reference voltage V1.25, and a pin XO connected with a reference voltage V2.0.

7. The non-invasive electronic apparatus for measuring blood pressure according to claim 1, further comprising a precise amplifier having an input terminal connected with an output of the first pressure sensor, wherein the precise amplifier outputs both a pulse signal amplified by a two-stage amplification circuit and a pressure signal to an A/D converter circuit.

8. The non-invasive electronic apparatus for measuring blood pressure according to claim 7, further comprising a gain control and reference voltage circuit which has an output terminal connected with the two-stage amplification circuit; the two-stage amplification circuit comprises a preamplifier and a postamplifier which are connected in series, wherein an input terminal of the preamplifier or the postamplifier is connected with a first resistor, while a second resistor is in parallel connected with or not connected with the first resistor via the gain control and reference voltage circuit, which is determined by pins A, B and C of the gain control and reference voltage circuit controlled by SETP and AN_MODE signals from the first microprocessor.

* * * * *